(12) United States Patent  (10) Patent No.: US 8,480,589 B2
Sato  (45) Date of Patent: Jul. 9, 2013

(54) ULTRASOUND IMAGING METHOD AND APPARATUS TO SUPPRESS MULTIPLE ECHOES INSIDE THE CRANIUM

(75) Inventor: Tomoo Sato, Ashigara-kami-gun (JP)

(73) Assignee: FUJIFILM Corporation, Tokyo (JP)

( * ) Notice: Subject to any disclaimer, the term of this patent is extended or adjusted under 35 U.S.C. 154(b) by 75 days.

(21) Appl. No.: 13/070,861

(22) Filed: Mar. 24, 2011

(65) Prior Publication Data

US 2011/0245674 A1  Oct. 6, 2011

(30) Foreign Application Priority Data

Mar. 31, 2010 (JP) ................................ 2010-080234

(51) Int. Cl.
*A61B 8/00* (2006.01)
(52) U.S. Cl.
USPC ............................... 600/451; 600/443; 601/2
(58) Field of Classification Search
USPC ................. 128/916, 915; 600/437, 427, 451, 600/443; 601/2
See application file for complete search history.

(56) References Cited

U.S. PATENT DOCUMENTS

| 6,387,051 B1* | 5/2002 | Ragauskas et al. ........... 600/438 |
| 6,666,833 B1* | 12/2003 | Friedman et al. ................. 601/2 |
| 7,101,337 B2* | 9/2006 | Aubry et al. .................. 600/447 |
| 2008/0262350 A1* | 10/2008 | Unger .......................... 600/439 |

FOREIGN PATENT DOCUMENTS

JP  2007-117165 A  5/2007

* cited by examiner

*Primary Examiner* — Long V. Le
*Assistant Examiner* — Helene Bor
(74) *Attorney, Agent, or Firm* — Sughrue Mion, PLLC

(57) ABSTRACT

An ultrasound imaging method comprises the steps of: transmitting a prescanning ultrasonic beam toward a subject and measuring an ultrasonic echo from a bone structure inside a cranium in advance; determining a transfer function of an ultrasonic wave in the cranium based on the measured said ultrasonic echo; transmitting an imaging ultrasonic beam toward the subject; generating a cancelling ultrasonic beam having an opposite phase as an ultrasonic echo reflected by the inner surface of the cranium due to said imaging ultrasonic beam, based on said transfer function; receiving an ultrasonic echo from the subject while cancelling said ultrasonic echo from the bone structure inside the cranium by transmitting the cancelling ultrasonic beam in accordance with the ultrasonic echo from the bone structure inside the cranium due to said imaging ultrasonic beam; and generating an ultrasound image of the subject.

10 Claims, 3 Drawing Sheets ured by the ultrasound probe is known. In recent years, ultrasound

ULTRASOUND IMAGING METHOD AND APPARATUS TO SUPPRESS MULTIPLE ECHOES INSIDE THE CRANIUM

BACKGROUND OF THE INVENTION

The present invention relates to an ultrasound imaging method and apparatus which produce ultrasound images, and in particular, to an ultrasound imaging method and apparatus which produce intracranial ultrasound images.

Ultrasound imaging which produces ultrasound images by transmitting an imaging ultrasonic beam from an ultrasound probe toward a subject and receiving the ultrasonic echo reflected by the subject is known. In recent years, ultrasound imaging has been applied to intracranial observation. For example, intracranial ultrasound images have been produced by transmitting an imaging ultrasonic beam toward a subject inside a cranium from a thin place on the cranium such as the temple.

In this type of intracranial ultrasound imaging, multiple echoes occur, wherein part of the imaging ultrasonic beam transmitted inside the cranium is repeatedly reflected by the inner surface of the cranium and so forth. Multiple echoes of the imaging ultrasonic beam result in noise in the produced ultrasound image, and also have the risk of affecting brain tissue.

Thus, in JP 2007-117165 A, for example, a technique is proposed whereby, in multiple echoes occurring between the surface of the ultrasound probe and inside the body, noise in the ultrasound image is reduced by cancelling out echoes reflected by the ultrasound probe.

However, even if the echo reflected by the surface of the ultrasound probe is cancelled out, multiple echoes of the ultrasonic echo occurring on the inner surface of the cranium still exist, and there is risk that the remaining ultrasonic echoes affect brain tissue.

SUMMARY OF THE INVENTION

An object of the present invention is to provide an ultrasound imaging method and apparatus which resolve such problems of the past, and can suppress multiple echoes of ultrasonic echo inside the cranium.

An ultrasound imaging method according to the present invention comprises the steps of:

transmitting a prescanning ultrasonic beam toward a subject and measuring an ultrasonic echo from a bone structure inside a cranium in advance;

determining a transfer function of an ultrasonic wave in the cranium based on the measured said ultrasonic echo;

transmitting an imaging ultrasonic beam toward the subject;

generating a cancelling ultrasonic beam having an opposite phase as an ultrasonic echo reflected by the inner surface of the cranium due to said imaging ultrasonic beam, based on said transfer function;

receiving an ultrasonic echo from the subject while cancelling said ultrasonic echo from the bone structure inside the cranium by transmitting said cancelling ultrasonic beam in accordance with the ultrasonic echo from the bone structure inside the cranium due to said imaging ultrasonic beam; and generating an ultrasound image of the subject based on the ultrasonic echo received from the subject.

An ultrasound imaging apparatus according to the present invention comprises:

echo measurement means which transmits a prescanning ultrasonic beam toward a subject and measures an ultrasonic echo from a bone structure inside a cranium;

transfer function calculation means which determines a transfer function of an ultrasonic wave in the cranium based on said ultrasonic echo measured by said echo measurement means;

imaging means which transmits an imaging ultrasonic beam toward a subject and receives ultrasonic echoes from the subject to generate an ultrasound image of the subject; and cancelling ultrasonic beam transmission means which, based on said transfer function, generates a cancelling ultrasonic beam having an opposite phase as an ultrasonic echo reflected by the inner surface of the cranium due to said imaging ultrasonic beam, and transmits it in accordance with the ultrasonic echo from the bone structure inside the cranium due to said imaging ultrasonic beam.

DETAILED DESCRIPTION OF THE INVENTION

The present invention is described in detail hereinafter based on a preferred embodiment shown in the accompanying drawings.

Figure 1:
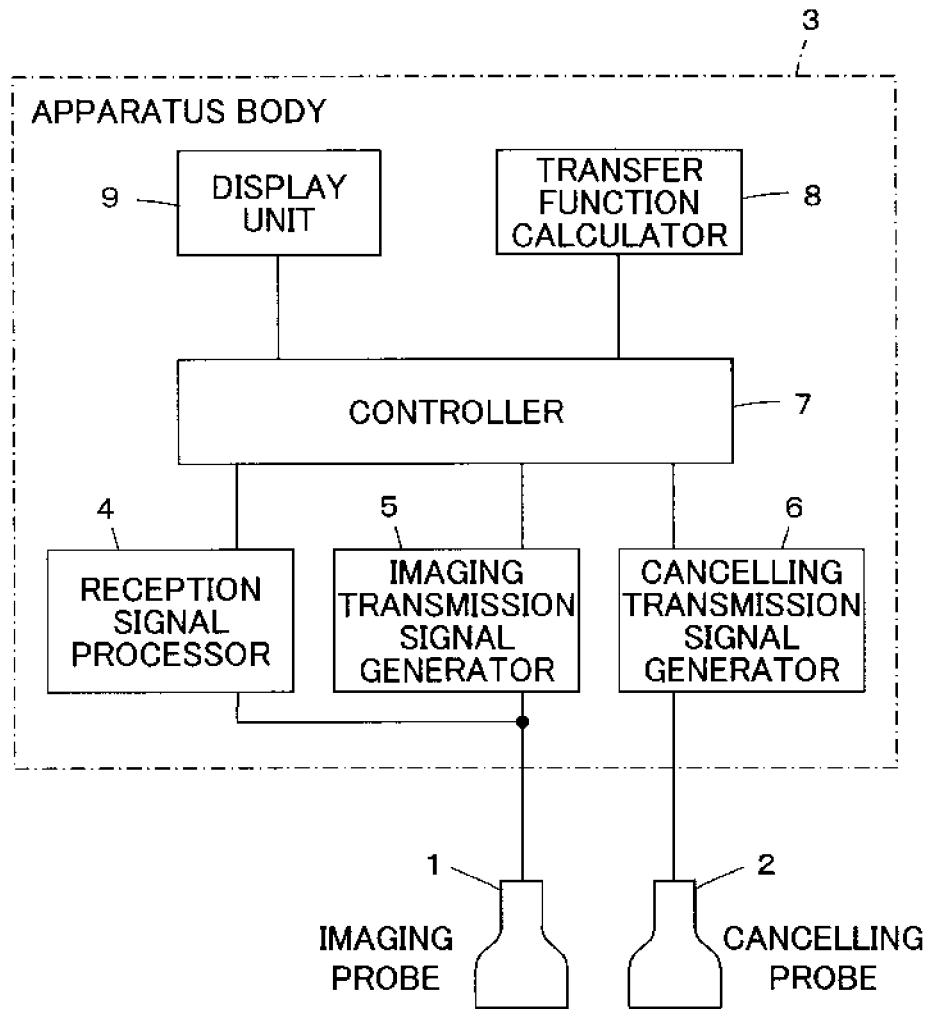
FIG. 1 is a block diagram illustrating a configuration of a ultrasound imaging apparatus according to one embodiment of the present invention.

FIG. 1 illustrates a configuration of an ultrasound imaging apparatus according to one embodiment of the present invention. The ultrasound imaging apparatus comprises an imaging probe 1, a cancelling probe 2 and an apparatus body 3.

The imaging probe 1 and the cancelling probe 2 each have a plurality of ultrasound transducers lined up in an array. When imaging, the imaging probe 1 transmits an imaging ultrasonic beam toward a subject and receives ultrasonic echoes reflected by the subject, and the cancelling probe 2 transmits cancelling ultrasonic beams toward the inside of a cranium. When prescanning, the imaging probe 1 transmits a prescanning ultrasonic beam toward the inside of the cranium and receives ultrasonic echoes from a bone structure inside the cranium.

The apparatus body 3 comprises a reception signal processor 4 connected to the imaging probe 1, an imaging transmission signal generator 5 connected to the imaging probe 1, and a cancelling transmission signal generator 6 connected to the cancelling probe 2.

Reception signals corresponding to the ultrasonic echoes received by the imaging probe 1 are input from the imaging probe 1 to the reception signal processor 4. The imaging transmission signal generator 5 generates imaging transmission signals and prescanning transmission signals, and outputs them to the imaging probe 1. The cancelling transmission signal generator 6 generates cancelling transmission signals corresponding to cancelling ultrasonic beams having the opposite phase as the ultrasonic echoes reflected by the inner surface of the cranium, and outputs them to the cancelling probe 2.

The reception signal processor 4, the imaging transmission signal generator 5 and the cancelling transmission signal generator 6 are each connected to a controller 7. The controller 7 controls input and output of signals to and from the parts in the apparatus body 3.

A transfer function calculator 8 and a display unit 9 are also each connected to the controller 7. The transfer function calculator 8 determines a transfer function of ultrasonic waves that propagate through the cranium, based on the ultrasonic echoes from the bone structure inside the cranium obtained in advance in prescanning. Here, the transfer function includes a propagation delay quantity and a waveform deformation quantity (including amplitude, phase, etc.) of the ultrasonic wave arising due to a thickness of the cranium at respective positions on the cranium.

The display unit 9 displays an ultrasound image produced based on the reception signals corresponding to the ultrasonic echoes received by the reception signal processor 4.

The echo measurement means of the present invention is constructed of the above-described imaging probe 1, the reception signal processor 4 and the imaging transmission signal generator 5, and the cancelling ultrasonic beam transmission means of the present invention is constructed of the cancelling probe 2 and the cancelling transmission signal generator 6.

Next, the operation of the ultrasound imaging apparatus illustrated in FIG. 1 will be described.

Figure 2:
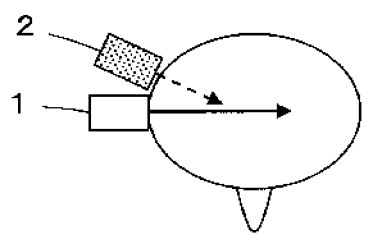
FIG. 2 is a block diagram illustrating an arrangement position of probes used in the embodiment.

First, as shown in FIG. 2, the imaging probe 1 is arranged at a specified position on the head, and the cancelling probe 2 is arranged at a position adjacent to the imaging probe 1. When the imaging probe 1 and the cancelling probe 2 have been arranged, the imaging transmission signal generator 5 generates a prescanning transmission signal, and outputs it to the imaging probe 1. As a result, a prescanning ultrasonic beam is transmitted from the imaging probe 1 toward the inner surface of the cranium, and prescanning of the bone structure inside the cranium is performed.

Figure 3:
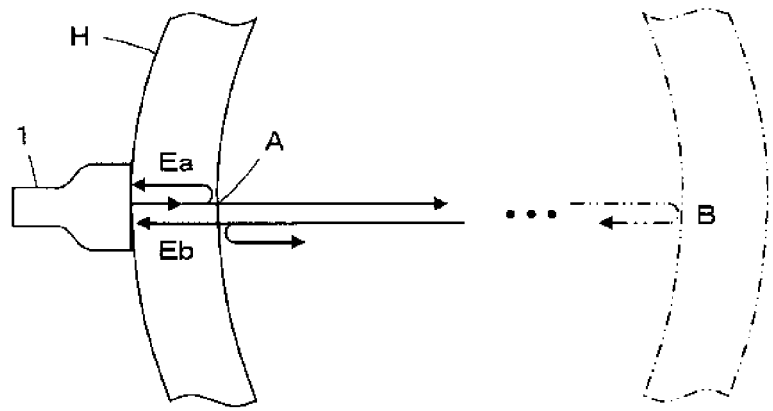
FIG. 3 is a drawing illustrating a state of ultrasonic beam propagation in prescanning.

As shown in FIG. 3, the prescanning ultrasonic beam transmitted from the imaging probe 1 propagates through the cranium H and reaches point A on the inner surface of the cranium, and an ultrasonic echo Ea reflected at point A on the inner surface of the cranium and returned is received by the imaging probe 1. Here, when the ultrasonic wave propagates through the cranium H, deformation of the waveform caused by the thickness of the cranium H occurs due to propagation delay and attenuation.

On the other hand, a part of the prescanning ultrasonic beam that passed through point A on the cranium H reaches point B on the inner surface of the cranium on a side opposite the side where the imaging probe 1 is arranged, and an ultrasonic echo Eb reflected from its bone structure again reaches point A on the cranium H. The ultrasonic echo Eb that passed through point A on the cranium H is received by the imaging probe 1. Also, a part of the ultrasonic echo Eb is additionally reflected at point A on the cranium H.

Reception signals for the ultrasonic echoes Ea and Eb from the bone structure received by the imaging probe 1 are input into the reception signal processor 4. When the reception signal processor 4 outputs reception signals corresponding to the input ultrasonic echoes Ea and Eb to the controller 7, the controller 7 outputs those reception signals to the transfer function calculator 8.

Based on the reception signal of the ultrasonic echo Ea received from the bone structure, the transfer function calculator 8 determines the transfer function of the ultrasonic wave in the cranium H. That is, the transfer function calculator 8 determines the transfer function of the ultrasonic wave in the cranium H based on a time of transmission and a waveform of the prescanning ultrasonic beam transmitted from the imaging probe 1, and on a time of reception and a waveform of the ultrasonic echo Ea received by the imaging probe 1. Also, the transfer function calculator 8 determines a transit time required for the ultrasonic beam transmitted from the imaging probe 1 to be reflected at point B on the cranium H and reach point A on the cranium H, based on the times of reception of ultrasonic echoes Ea and Eb received by the imaging probe 1. The propagation delay quantity, the waveform deformation quantity and the transit time determined in this way are output to the controller 7, and from the controller 7 they are output to the cancelling transmission signal generator 6.

Figure 4:
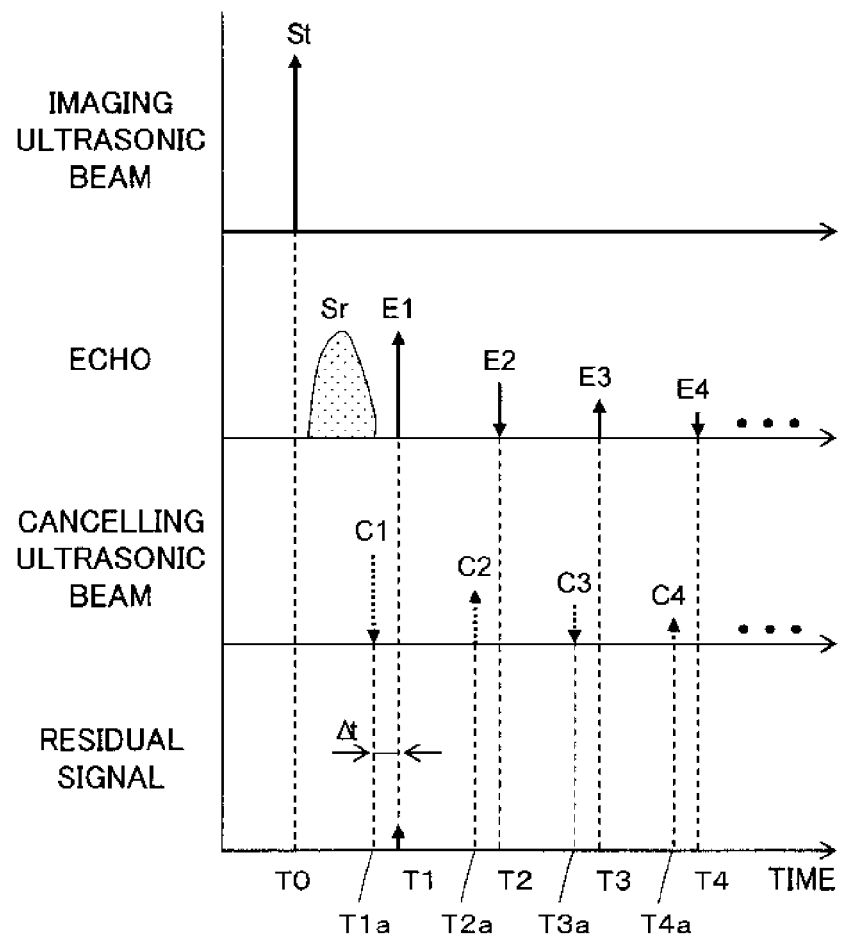
FIG. 4 is a drawing illustrating a state where an ultrasonic echo from a cranium is cancelled out.

Next, imaging of the subject inside the cranium H will be described. As shown in FIG. 4, the imaging transmission signal generator 5 generates an imaging transmission signal and outputs it to the imaging probe 1, and from the imaging probe 1, an imaging ultrasonic beam St corresponding to the imaging transmission signal is transmitted at time T0.

The imaging ultrasonic beam St propagates through the cranium H, passing through point A on the cranium H, and reaches the subject such as a blood vessel inside the cranium H. A ultrasonic echo Sr reflected by the subject again passes through point A on the cranium H and is received by the imaging probe 1. On the other hand, the part of the imaging ultrasonic beam St that propagated through the subject reaches point B on the cranium H, and the first echo E1 reflected from its bone structure again reaches point A on the cranium H at time T1.

At this time, based on the propagation delay and transit time input from the transfer function calculator 8 via the controller 7, the cancelling transmission signal generator 6 determines a time Δt for the ultrasonic wave to reach from the cancelling probe 2 to point A on the cranium H, and determines a time T1 at which the first echo E1 reaches point A on the cranium H. Then, the cancelling transmission signal generator 6 transmits a cancelling ultrasonic beam having the opposite phase as the first echo E1, from the cancelling probe 2 at time T1a, which is Δt earlier than time T1 at which the first echo E1 reaches point A of the cranium H. Here, based on the waveform deformation quantity of the ultrasonic wave at the cranium H determined by the transfer function calculator 8, the cancelling transmission signal generator 6 transmits a cancelling ultrasonic beam C1 having the opposite phase as the first echo E1 and having an amplitude so as to leave the first echo E1 to the degree required to create an image. Note that the degree required to create an image is the amount at which the position of the bone structure can be confirmed without being buried in noise when an image of the first echo E1 is created.

Figure 5:
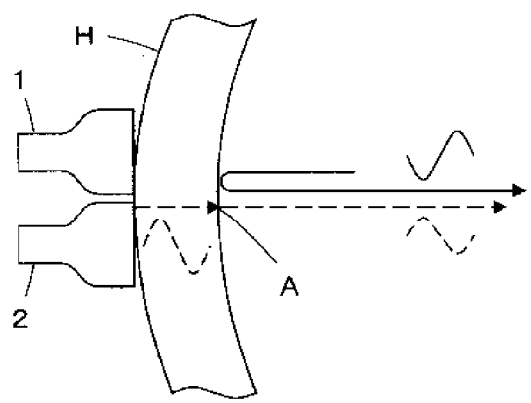
FIG. 5 is a drawing illustrating a state of ultrasonic beam propagation in imaging.

In this way, as shown in FIG. 5, the cancelling ultrasonic beam C1 transmitted from the cancelling probe 2 propagates through the cranium H while being attenuated, and at point A on the cranium H, it interferes with the first echo E1 by a waveform having the opposite phase as the first echo E1 and having an amplitude so as to leave the first echo E1 to the degree required to create an image.

Also, the part of the first echo E1 that was reflected without passing through point A on the cranium H again reaches point B on the cranium H, and a second echo E2 reflected here reaches point A on the cranium H at time T2. Similarly, the cancelling transmission signal generator 6 transmits a cancelling ultrasonic beam C2, so as to completely cancel out the second echo E2, from the cancelling probe 2 at time T2a which is Δt earlier than time T2 at which the second echo E2 reaches point A on the cranium H, thereby completely cancelling out the second echo E2 which reaches point A on the cranium H. Furthermore, in the case where the second echo E2 cannot be completely cancelled out and a third echo E3, a fourth echo E4, etc. are generated, they can be respectively cancelled out by it transmitting cancelling ultrasonic beams C3, C4, etc., so as to completely cancel out the third echo E3, fourth echo E4, etc., from the cancelling probe 2 at times T3a, T4a, etc. which are Δt earlier than times T3, T4, etc. at which the third echo E3, the fourth echo E4, etc. reach point A on the cranium H.

In this way, by reducing the first echo E1 and completely cancelling out echoes E3, E4, etc. beyond the second echo E2, it is possible to suppress multiple echoes of ultrasonic echo inside the cranium H.

Thus, by transmitting cancelling ultrasonic beams, the majority of the ultrasonic echoes reflected and returned at point B on the cranium H are cancelled out, and, as shown in FIG. 4, a residual signal of these ultrasonic echoes is equivalent only to the difference between the first echo E1 and the cancelling ultrasonic beam C1. This residual signal and the reception signal corresponding to the ultrasonic echo Sr of the subject are output from the imaging probe 1 to the reception signal processor 4, and the reception signal processor 4 outputs them to the controller 7. The controller 7 outputs the input reception signal corresponding to the ultrasonic echo Sr of the subject and the residual signal to the display unit 9, and the display unit 9 generates and displays an ultrasound image based on the input signals. In this way, an image obtained by reducing the first echo E1, which is later than the ultrasonic echo from the deepest part of the image display region inside the cranium, and cancelling out the second echo E2, the third echo E3, the fourth echo E4, etc. is displayed on the display unit 9.

According to the ultrasound imaging apparatus of this embodiment, it is possible to suppress multiple echoes of ultrasonic echo inside the cranium H by reducing the first echo E1 and completely cancelling out the echoes E3, E4, etc. beyond the second echo E2.

Figure 6:
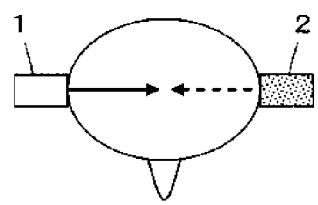
FIG. 6 is a drawing illustrating an arrangement position of probes in a modification of the embodiment.
Figure 7:
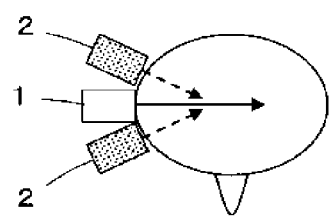
FIG. 7 is a drawing illustrating an arrangement position of probes in another modification of the embodiment.

Note that in this embodiment, the arrangement of the cancelling probe 2 on the head is not particularly limited, provided that the imaging ultrasonic beam can be transmitted from the imaging probe 1 and the ultrasonic echo from the bone structure inside the cranium H can be cancelled out by the cancelling ultrasonic beam. For example, as shown in FIG. 6, the cancelling probe 2 may be arranged at a position which opposes the imaging probe 1 arranged on the head. Also, as shown in FIG. 7, ultrasonic echo from the bone structure which diffuses and propagates inside the cranium H can be cancelled out with high precision by arranging two cancelling probes 2 adjacent to the imaging probe 1 arranged on the head.

Figure 8:
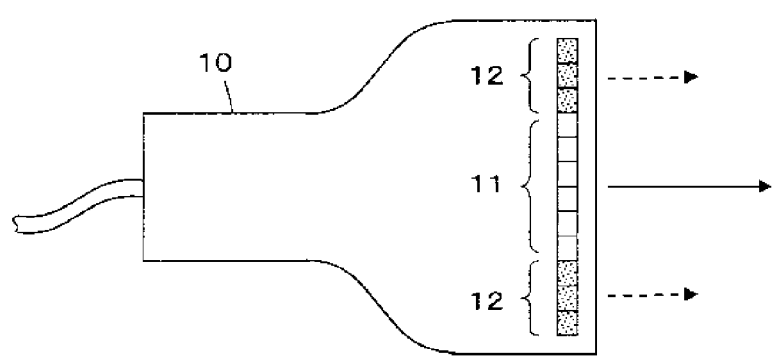
FIG. 8 is a drawing illustrating a configuration of a probe used in still another modification of the embodiment.

Furthermore, it may be configured such that the cancelling probe 2 is omitted, the imaging probe 1 and the cancelling transmission signal generator 6 are connected, and the cancelling transmission signal generator 6 transmits cancelling ultrasonic beams from some of a plurality of ultrasonic transducers of the imaging probe 1. For example, as shown in FIG. 8, an imaging probe 10 has a plurality of imaging transducers 11 arranged in the center, and a plurality of cancelling transducers 12 arranged on both sides sandwiching the plurality of imaging transducers 11. By so doing, it is possible to suppress multiple echoes of ultrasonic echo inside the cranium H using only the imaging probe 10. It is also possible to configure the imaging probe 10 such that a plurality of cancelling transducers 12 are adjacent to only one of the plurality of imaging transducers 11.

Also, in this embodiment, an imaging ultrasonic beam and a prescanning ultrasonic beam are transmitted from the imaging probe 1 and a cancelling ultrasonic beam is transmitted from the cancelling probe 2, but the method of transmitting the ultrasonic beams is not particularly limited, provided that the first echo can be cancelled out by the cancelling ultrasonic beam. For example, the imaging ultrasonic beam may be transmitted from the imaging probe 1, and the prescanning ultrasonic beam and cancelling ultrasonic beam may be transmitted from the cancelling probe 2.

What is claimed is:

1. An ultrasound imaging method comprising the steps of:
transmitting a prescanning ultrasonic beam toward a subject inside a cranium and
measuring an ultrasonic echo reflected by a bone structure forming the cranium in advance of imaging the subject within the cranium;
determining a transfer function of the measured ultrasonic echo in the bone structure forming the cranium;
transmitting an imaging ultrasonic beam toward the subject;
generating a cancelling ultrasonic beam, said cancelling ultrasonic beam having an opposite phase with respect to a bone-reflected ultrasonic echo reflected by the bone structure forming the cranium due to said imaging ultrasonic beam, based on said transfer function;
receiving a subject-reflected ultrasonic echo from the subject inside the cranium due to the imaging ultrasonic beam while cancelling the bone-reflected ultrasonic echo reflected by the bone structure forming the cranium by transmitting said cancelling ultrasonic beam in accordance with the bone-reflected ultrasonic echo reflected by the bone structure forming the cranium due to said imaging ultrasonic beam; and
generating an ultrasound image of the subject based on the subject-reflected ultrasonic echo received from the subject.

2. The ultrasound imaging method according to claim 1, wherein said cancelling ultrasonic beam is transmitted in accordance with the bone-reflected ultrasonic echo reflected by the bone structure forming the cranium which is generated later than the ultrasonic echo from the deepest part of an image display region inside the cranium after said imaging ultrasonic beam was transmitted.

3. The ultrasound imaging method according to claim 1, wherein only a first echo is left to the degree required to create an image, among the bone-reflected ultrasonic echoes reflected by the bone structure forming the cranium, by transmitting the cancelling ultrasonic beam.

4. The ultrasound imaging method according to claim 1, wherein said prescanning ultrasonic beam and said imaging ultrasonic beam are transmitted from a probe while said cancelling ultrasonic beam is transmitted from another probe different from the probe.

5. The ultrasound imaging method according to claim 1, wherein said prescanning ultrasonic beam and said imaging ultrasonic beam are transmitted from a probe, and said cancelling ultrasonic beam is transmitted from transducers of some of ultrasound probe elements contained in the probe.

6. An ultrasound imaging apparatus comprising;
echo measurement device configured to transmit a prescanning ultrasonic beam toward a subject inside a cranium and measures an ultrasonic echo reflected by a bone structure forming the cranium;
transfer function calculation device configured to determine a transfer function of an ultrasonic wave in the bone structure forming the cranium based on said ultrasonic echo measured by said echo measurement device;
imagining means for transmitting an imaging ultrasonic beam toward the subject inside a cranium and receiving a subject-reflected ultrasonic echo from toward the subject inside the cranium to generate an ultrasound image of the subject; and
cancelling ultrasonic beam transmission device configured to generate, based on said transfer function a cancelling ultrasonic beam having an opposite phase as bone-reflected ultrasonic echo reflected by the bone structure forming the cranium due to said imaging ultrasonic beam, and transmits it in accordance with the bone-reflected
ultrasonic echo reflected by the bone structure forming the cranium due to said imaging ultrasonic beam.

7. The ultrasound imaging apparatus according to claim 6, wherein said cancelling ultrasonic beam transmission device transmits said cancelling ultrasonic beam in accordance with the bone-reflected ultrasonic echo reflected by the bone structure forming the cranium which is generated later than the ultrasonic echo from the deepest part of an image display region inside the cranium after transmission of said imaging ultrasonic beam.

8. The ultrasound imaging apparatus according to claim 6, wherein said cancelling ultrasonic beam transmission device transmits said cancelling ultrasonic beam to leave only a first echo to the degree required to create an image, among the bone-reflected ultrasonic echoes from the bone structure forming the cranium.

9. The ultrasound imaging apparatus according to claim 6, wherein:
said imaging means comprises an imaging probe for transmitting said imaging ultrasonic beam; and
said cancelling ultrasonic beam transmission device comprises a cancelling probe for transmitting said cancelling ultrasonic beam, which differs from said imaging probe.

10. The ultrasound imaging apparatus according to claim 6, wherein:
said imaging means comprises an imaging probe for transmitting said imaging ultrasonic beam; and
said cancelling ultrasonic beam transmission device transmits said canceling ultrasonic beam from transducers of some of ultrasound probe elements contained in said imaging probe.

* * * * *